(12) United States Patent
Busch et al.

(10) Patent No.: US 9,102,689 B2
(45) Date of Patent: Aug. 11, 2015

(54) PROCESS FOR THE PREPARATION OF BORONIC ACID INTERMEDIATES

(71) Applicant: Hoffmann-La Roche Inc., Nutley, NJ (US)

(72) Inventors: Torsten Busch, Frankfurt am Main (DE); Michael Nonnenmacher, Leimen (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/269,334

(22) Filed: May 5, 2014

(65) Prior Publication Data

US 2014/0330008 A1 Nov. 6, 2014

(30) Foreign Application Priority Data

May 6, 2013 (EP) ..................................... 13166587

(51) Int. Cl.
*C07F 5/02* (2006.01)
*C07D 495/04* (2006.01)
*C07D 491/048* (2006.01)

(52) U.S. Cl.
CPC ............ *C07F 5/025* (2013.01); *C07D 491/048* (2013.01); *C07D 495/04* (2013.01)

(58) Field of Classification Search
CPC ........ C07F 5/02; C07F 5/025; C07F 491/048; C07F 495/04
See application file for complete search history.

(56) References Cited

U.S. PATENT DOCUMENTS 8,895,729 B2 * 11/2014 Babu et al. ..................... 544/117
2008/0269523 A1 * 10/2008 Kressierer et al. ................ 564/8

OTHER PUBLICATIONS

K.M. Clapham et al., European Journal of Organic Chemistry, 5712-5716 (2007).*
S.D. Walker et al., 43 Angewandte Chemie International Edition, 1871-1876 (2004).*
T. Barder et al., 127 Journal of the American Chemical Society, 4685-4696 (2005).*
J.J. Li, Name Reactions a Collection of Detailed Mechanisms and Synthetic Applications (2009).*
N. Miyaura et al., Tetrahedron Letters, 3437-3440 (1978).*

* cited by examiner

*Primary Examiner* — Alexander R Pagano
(74) *Attorney, Agent, or Firm* — Alex Andrus; Genetech, Inc.

(57) ABSTRACT

The present invention relates to a process for the preparation of 2-amino-pyrimidine-5-boronic acid of formula (I).

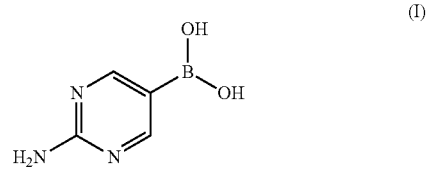

or salts or esters thereof.

19 Claims, No Drawings

PROCESS FOR THE PREPARATION OF BORONIC ACID INTERMEDIATES

This non-provisional application claims the benefit under 35 USC §119 of European Patent application 13166587.9, filed 6 May 2013, which is incorporated by reference in entirety.

The present invention relates to an improved process for the preparation of 2-amino-pyrimidine-5-boronic acid of formula (I)

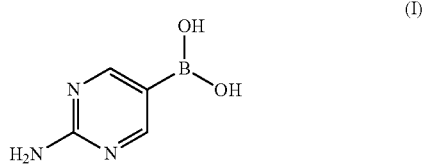

or salts or esters thereof.

The 2-amino-pyrimidine-5-boronic acid is an important building block for the preparation of pure active pharmaceutical ingredients (APIs) used for the treatment of oncological disorders as described in WO2008/070740.

Boronic acids are used extensively in organic chemistry as chemical building blocks and intermediates predominantly in the Suzuki-coupling. The Suzuki-coupling is the palladium-catalyzed cross coupling between organoboronic acid and halides (N. Miyaura, Tyanagi and A. Suzuki, Synth. Commun., 1981, 11, 513; Wikipedia). Aryl triflates are also effective coupling partners (T. Ohe, N. Miyaura and A. Suzuki J. Org. Chem. 1993, 58, 2201). In part due to the ease of preparation, high stability and low toxicity of such boronic acids, there is currently widespread interest in applications of such boronic acids and their use in Suzuki-coupling.

Organic arylboronic and heteroarylboronic acids, and their derivatives, can be obtained by different synthetic routes: by cross-coupling of bis(pinacolato)diboron ($B_2pin_2$) with aryl halides and vinyl halides (Miyaura borylation reaction) or by conversion of aryllithium or arylmagnesium compounds with a boronic acid trialkyl ester followed by acid hydrolysis (T. Leermann, F. R. Leroux, F. Colobert, Org. Lett., 2011, 13, 4479-4481).

The above described synthetic approaches for the preparation of organic arylboronic and heteroarylboronic acids have some limitations mainly linked to the presence of some functional groups which are not compatible with the employed reaction conditions. So, for example, the presence of an amino group interferes with the formation of the organometallic compounds. This interference could be theoretically overcome using a large excess of reagent(s) with negative impacts on the costs of the process and in the workup of the reaction.

Several additional synthetic strategies were applied for the preparation of aminoaryl and aminoheteroaryl boronic acids and esters using different amino protective groups.

The Chinese patent application CN102367260A describes the possibility to use di-tert butyl dicarbonate derivatives (t-BOC derivatives) of bromo heteroaryl amine compounds. The Chinese patent application CN102399235 describes the use of di-tert butyl dicarbonate derivatives (t-BOC derivatives) in the preparation of 2-amino-5-pyrimidine-boronic acid pinacol ester via a 2-amino-pyrimidine-5-boronic acid.

Moreover in literature are also described the possibility to use, as alternative approaches, the protection of the amino group as N,N-dibenzyl derivative, a functional group that can be removed by hydrogenation (U.S. Pat. No. 7,196,219B2) or the moisture unstable N, N-trimethylsilyl derivative (Tetrahedron Letters (2003) 44(42), 7719-7722).

The scaling up of these synthetic approaches has some important drawbacks, because the compounds used are very toxic, flammable, moisture unstable and difficult to handle.

US2008/0269523 describes the preparation of aminoaryl and aminoheteroaryl boronic acids in which optionally substituted aminoaryl or aminoheteroaryl compounds are protected at the nitrogen site as an imine derivative via condensation with a carbonyl compound and subsequent reaction with a suitable boron compound, whereby after reconditioning and removal of the protective group the corresponding boronic acid, the anhydride or the boronic acid ester thereof is obtained. In particular, the preparation of the intermediate imine derivative is not or only to some extent possible for some aminoaryl or aminoheteroaryl compounds, due to the low reactivity of the amino-group, solubility problems of such precursor molecules and low stability of the intermediate imine derivatives under the reaction conditions (e.g. the presence of water). This is in particular true for bromo heteroaryl amine compounds, such as 2-amino-5-bromo pyrimidine e.g. when the reaction is performed in toluene. In addition, the yields of the conversion of the imine derivative to the final aminoaryl or aminoheteroaryl boronic acids were very low. In cases of scale-up, the overall yield of the reaction is in particular low and the reaction time very long. In some cases the processes show problems with reproducibility.

The object of the present invention is an improved process for the preparation of 2-amino-pyrimidine-5-boronic acid which overcomes the problem of the low reactivity of the amino-group, the solubility problems for the precursor molecules, stability problems of the intermediate imine derivative, and the low yields of the conversion of the imine derivative to the final aminoaryl or aminoheteroaryl boronic acids by using safe, non-toxic and easy to handle reactants.

The invention may be described in more detail as follows.

The present invention relates to a process for the preparation of a compound of formula (I)

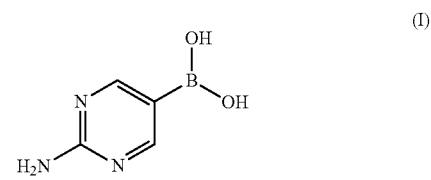

or salts or esters thereof, comprising
a) adding a compound of formula (II)

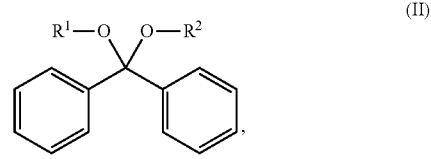

wherein $R^1$ and $R^2$ each independently is $C_{1-6}$ alkyl, to a solution of a compound of formula (III)

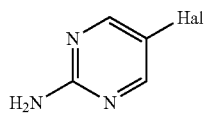

and an immobilized acidic catalyst in a polar aprotic organic solvent with a boiling point above 100° C., wherein Hal is F, Cl, Br or I;
to form a compound of formula (IV)

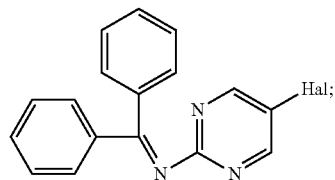

b) reacting a mixture of a compound of formula (IV) and a compound of formula (V) with a metalation reagent

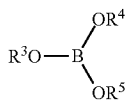

wherein $R^3$, $R^4$ and $R^5$ each independently is $C_{1-6}$ alkyl;
in a polar aprotic organic solvent at a temperature of −90° C. to −95° C.
to a compound of formula (VI)

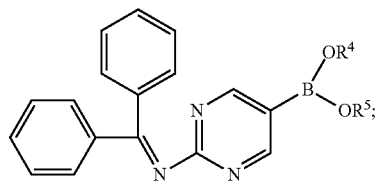

and
c) hydrolyzing the compound of formula (VI) to produce the compound of formula (I)

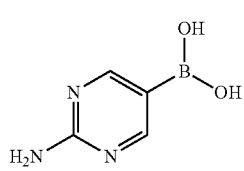

or salts or esters thereof.

In step a) the 2-amino-5-halogen-pyrimidine of formula (III) is protected through condensation with a highly reactive ketal (acetal) compound of formula (II). By introducing the protective group and forming the imino compound of formula (IV), the amine function cannot be deprotonated in the subsequent metalation step.

In one embodiment of the invention, the polar aprotic organic solvent in step a) has a boiling point above 110° C. In one embodiment of the invention, the polar aprotic organic solvent in step a) has a boiling point of 110° C.-180° C. In one embodiment of the invention, the polar aprotic organic solvent in step a) has a boiling point of 120° C.-130° C. In one embodiment of the invention, the polar aprotic organic solvent in step a) has a boiling point of 125° C.-129° C. In one embodiment of the invention, the polar aprotic organic solvent in step a) has a boiling point of 126-128° C. In one embodiment of the invention, the polar aprotic organic solvent in step a) has a boiling point of 127° C.

In one embodiment, the polar aprotic organic solvent in step a) is n-butylacetate. By using n-butylacetate as solvent, surprisingly, the degradation of precursor molecules is significantly lowered and the reaction better controllable.

In one embodiment the polar aprotic organic solvent in step b) is THF.

In one embodiment, the polar aprotic organic solvent in step a) is n-butylacetate and the polar aprotic organic solvent is step b) is THF.

In one embodiment of the invention, $R^1$ and $R^2$ are methyl.

In one embodiment of the invention, Hal is Br or I.

In one embodiment of the invention, Hal is Br.

In one embodiment of the invention, $R^3$, $R^4$ and $R^5$ are isopropyl.

In one embodiment of the invention, the immobilized acidic catalyst is a solid polymeric resin.

In one embodiment of the invention, the solid polymeric resin is a solid, macroreticular polymeric resin.

In one embodiment of the invention, the solid, macroreticular polymeric resin is a solid, macroreticular polymeric ion exchange resin.

In one embodiment of the invention, the solid, macroreticular polymeric ion exchange resin is a solid, strongly acidic, macroreticular polymeric ion exchange resin.

In one embodiment of the invention, the solid, macroreticular polymeric ion exchange resin is a solid, strongly acidic, sulfonic acid, macroreticular polymeric ion exchange resin.

In one embodiment of the invention, the solid, macroreticular polymeric resin is a solid, strongly acidic, sulfonic acid, macroreticular polymeric resin.

In one embodiment of the invention, the solid, strongly acidic, macroreticular polymeric ion exchange resin is based on crosslinked styrene divinylbenzene copolymers.

In one embodiment of the invention, the solid, strongly acidic, macroreticular polymeric resin is based on crosslinked styrene divinylbenzene copolymers.

In one embodiment of the invention, the solid strongly acidic, sulfonic acid, macroreticular polymeric ion exchange resin is based on crosslinked styrene divinylbenzene copolymers.

In one embodiment of the invention, the solid strongly acidic, sulfonic acid, macroreticular polymeric resin is based on crosslinked styrene divinylbenzene copolymers.

In one embodiment of the invention, the solid, strongly acidic macroreticular polymeric ion exchange resin is Amberlyst™.

In one embodiment of the invention, the solid, strongly acidic macroreticular polymeric resin is Amberlyst™.

In one embodiment of the invention, the Amberlyst™ is the H⁺ form.

In one embodiment of the invention, the Amberlyst™ is Amberlyst™ 15WET or Amberlyst™ 15DRY.

In one embodiment of the invention, the Amberlyst™ is Amberlyst™ 15WET.

In one embodiment of the invention, the Amberlyst™ is Amberlyst™ 15DRY.

In one embodiment of the invention, the Amberlyst™ is Amberlyst™ 15 DRY ($H^+$ form).

Surprisingly, by using such immobilized acidic catalyst, the degradation of the educts is significantly reduced.

In one embodiment of the invention, the immobilized acidic catalyst is washed one time or several times with n-butylacetate prior to use.

In one embodiment of the invention, the immobilized acidic catalyst is washed one time or several times with boiling n-butylacetate prior to use.

In one embodiment of the invention, the Amberlyst™ is washed one time or several times with n-butylacetate prior to use.

In one embodiment of the invention, the Amberlyst™ is washed one time or several times with boiling n-butylacetate prior to use.

In one embodiment of the invention, the Amberlyst™ 15 DRY is washed one time or several times with boiling n-butylacetate prior to use.

In one embodiment of the invention, the Amberlyst™ 15 WET is washed one time or several times with boiling n-butylacetate prior to use.

In one embodiment of the invention, the compound of formula (II) is dissolved in n-butylacetate. Addition of the reagent can be performed using a pump dosage system. In one embodiment, the mixture of the compound of formula (II) and n-butylacetate is stirred for at least 1 hour prior to use to get a homogenous solution.

In one embodiment of the invention, the reaction of the compound of formula (II) with the compound of formula (III) is performed at a temperature of 110° C. to 120° C. In one embodiment of the invention, the reaction of the compound of formula (II) with the compound of formula (III) is performed in a controlled way at a temperature of 114-120° C.

In one embodiment of the invention, a distillate (mainly methanol) is removed from the above reaction mixture to increase the yield.

The dialkyl ketal derivative of formula (II) can be obtained according to methods well known in the art, such as for example the method described in Greene T. W. et al. Protecting groups in Organic synthesis, Wiley, Third Edition or be purchased from commercial sources.

Surprisingly under the reaction conditions applied, the intermediate imine derivatives of formula (IV) are very stable.

In one embodiment of the invention, the compound of formula (IV) can be isolated by using purification techniques well known to those skilled in the art, such as precipitation and crystallization.

Using the aforementioned process, it is possible to obtain the imine derivatives of formula (IV) in a very pure form which is essential to perform the following reactions.

Step b) relates to the conversion of the protected 2-amino-5-halogen-pyrimidine derivative of formula (IV) to the protected compound of formula (VI) via metalation and reaction with a suitable borate ester, e.g. tri-isopropyl borate.

In one embodiment of the invention, the mixture of the compound of formula (IV) and the compound of formula (V) is prepared in dry THF. In one embodiment of the invention, 20-25% of the overall mixture is charged to a reservoir while 75-80% of the precursor solution is added as described below.

In one embodiment of the invention, the mixture of the compound of formula (IV) and the compound of formula (V); and the metalation reagent are added to a reservoir in an alternating order.

In one embodiment of the invention, the mixture of the compound of formula (IV) and the compound of formula (V); and the metalation reagent are added to a reservoir simultaneously.

In one embodiment of the invention, the simultaneous dosing is done in a way that the reaction is started with 20-25% of mixture of the compound of formula (IV) and the compound of formula (V) in the reservoir and the excess of such mixture is maintained as long as possible.

In one embodiment of the invention, the alternating dosing is done in a way that the reaction is started with 20% of the mixture of the compound of formula (IV) and the compound of formula (V), followed by 20% of the metalation agent and continued by dosing alternating in each step 20% of such mixture and the metalation agent to the reservoir, respectively.

Surprisingly, using the aforementioned dosage controlled reactions, precipitation of precursor molecules and side reactions can be significantly reduced or avoided.

In one embodiment the dosing is performed at a temperature below −90° C. In one embodiment of the invention, the dosing is performed at a temperature of −95° C. to −90° C. In one embodiment of the invention, the dosing is performed at a temperature of −90° C.

In one embodiment of the invention, the borate ester of formula (V) is tri-isopropyl borate.

In one embodiment of the invention, the metalation reagent in step b) is selected from primary or secondary alkyllithium compounds such as butyllithium, hexyllithium or cyclohexyllithium.

In one embodiment of the invention, the metalation reagent in step b) is n-butyllithium (n-BuLi).

In one embodiment of the invention, step 1c) is performed without isolation of the compound of formula (VI). In this step the protective group and the ester groups attached to the B-atom are removed by hydrolysis.

In one embodiment of the invention, the hydrolysis is achieved by the use of aqueous acids. In one embodiment of the invention, the hydrolysis is achieved by hydrolysis by using aqueous sulfuric or hydrochloric acid. In one embodiment of the invention, the hydrolysis is achieved by hydrolysis by using aqueous hydrochloric acid.

In one embodiment of the invention, the hydrolysis is performed at a pH of 1 to 2. In one embodiment of the invention, the hydrolysis is performed at a pH of 1.2 to 1.5.

In one embodiment of the invention, the 2-amino-pyrimidine-5-boronic acid is isolated as a salt. In one embodiment of the invention the salt is a hydrogen sulfate salt or a hydrochloride salt. In one embodiment of the invention, the compound is isolated as inner salt.

In one embodiment, MTBE is used in one or more steps of steps a), b) or c) in the working up phase.

One embodiment of the invention relates to a process for the preparation of a compound of formula (I)

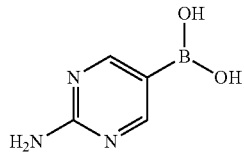
(I)

or salts or esters thereof,
characterized in that it comprises the steps of
a) adding a compound of formula (II)

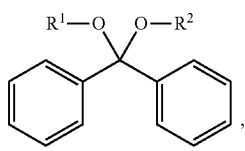
(II)

wherein $R^1$ and $R^2$ each independently is $C_{1-6}$ alkyl, to a solution of a compound of formula (III)

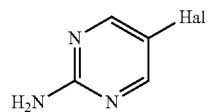
(III)

and a strongly acidic, sulfonic acid, macroreticular polymeric resin in n-butylacetate, wherein Hal is Br;
to form a compound of formula (IV)

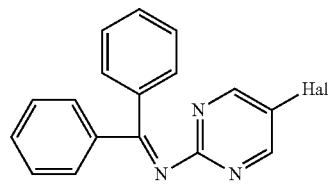
(IV)

and
b) reacting a mixture of a compound of formula (IV) and a compound of formula (V) with a metalation reagent

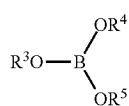
(V)

wherein $R^3$, $R^4$ and $R^5$ each independently is $C_{1-6}$ alkyl; in THF at a temperature of −90° C. to −95° C.

to a compound of formula (VI)

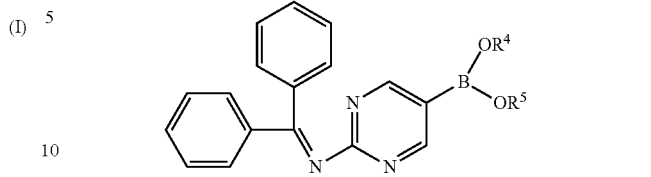
(VI)

and
c) hydrolyzing the compound of formula (VI) to produce the compound of formula (I)

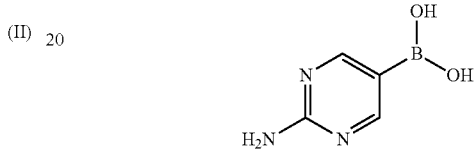
(I)

or salts or esters thereof

One embodiment of the invention relates to a process for the preparation of a compound of formula (I)

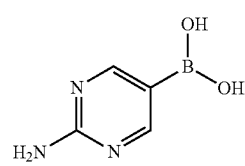
(I)

or salts or esters thereof,
characterized in that it comprises the steps of
a) adding a compound of formula (II)

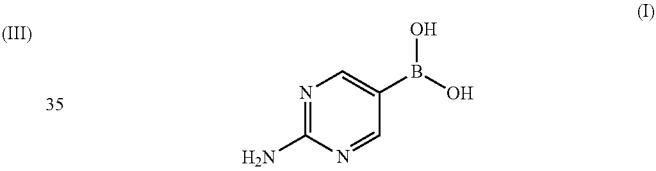
(II)

wherein $R^1$ and $R^2$ each independently is $C_{1-6}$ alkyl, to a solution of a compound of formula (III)

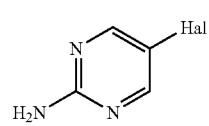
(III)

and a strongly acidic, sulfonic acid, macroreticular polymeric resin in n-butylacetate, wherein Hal is Br;

to form a compound of formula (IV)

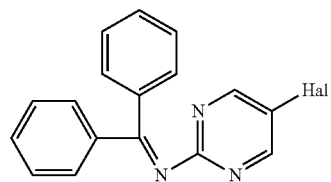

(IV)

and
b) reacting a mixture of a compound of formula (IV) and a compound of formula (V) with a metalation reagent

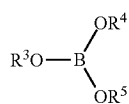

(V)

wherein $R^3$, $R^4$ and $R^5$ each independently is $C_{1-6}$ alkyl;
in THF at a temperature of $-90°$ C. to $-95°$ C.
to a compound of formula (VI)

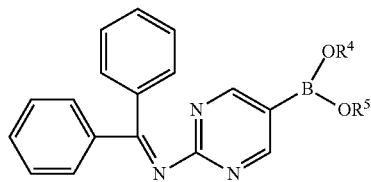

(VI)

and
c) hydrolyzing the compound of formula (VI) to produce the compound of formula (I)

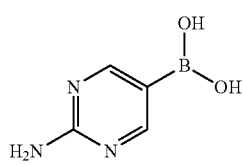

(I)

or salts or esters thereof, wherein such polymeric resin is washed one time or several times with boiling n-butylacetate prior to use.

One embodiment of the invention relates to a process for the preparation of a compound of formula (I)

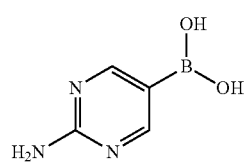

(I)

or salts or esters thereof, characterized in that it comprises the steps of
a) adding a compound of formula (II)

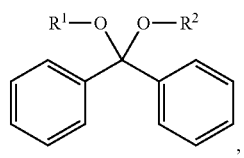

(II)

wherein $R^1$ and $R^2$ each independently is $C_{1-6}$ alkyl,
to a solution of a compound of formula (III)

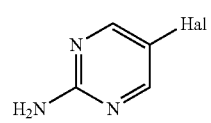

(III)

and a strongly acidic, sulfonic acid, macroreticular polymeric resin in n-butylacetate, wherein Hal is Br;
to form a compound of formula (IV)

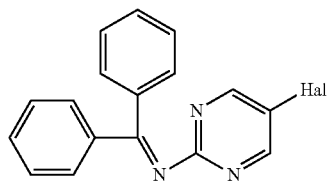

(IV)

and
b) reacting a mixture of a compound of formula (IV) and a compound of formula (V) with a metalation reagent

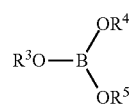

(V)

wherein $R^3$, $R^4$ and $R^5$ each independently is $C_{1-6}$ alkyl;
in THF at a temperature of $-90°$ C. to $-95°$ C.
to a compound of formula (VI)

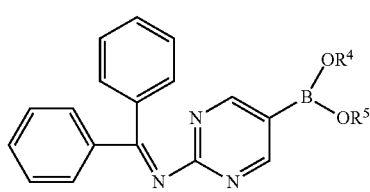

(VI)

and
c) hydrolyzing the compound of formula (VI) to produce the compound of formula (I)

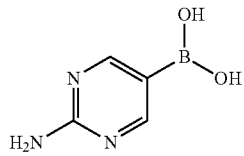

or salts or esters thereof, wherein the mixture of the compound of formula (IV) and the compound of formula (V); and the metalation reagent are added to a reservoir in an alternating order.

One embodiment of the invention relates to a process for the preparation of a compound of formula (I)

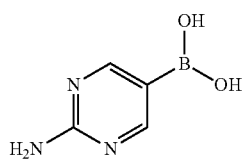

or salts or esters thereof,
characterized in that it comprises the steps of
a) adding a compound of formula (II)

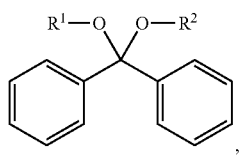

wherein $R^1$ and $R^2$ each independently is $C_{1-6}$ alkyl, to a solution of a compound of formula (III)

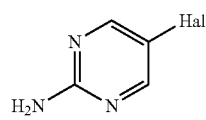

and a strongly acidic, sulfonic acid, macroreticular polymeric resin in n-butylacetate, wherein Hal is Br;
to form a compound of formula (IV)

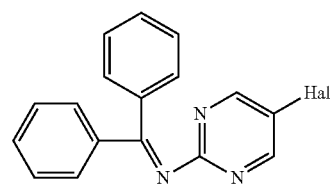

and
b) reacting a mixture of a compound of formula (IV) and a compound of formula (V) with a metalation reagent

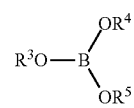

wherein $R^3$, $R^4$ and $R^5$ each independently is $C_{1-6}$ alkyl;
in THF at a temperature of −90° C. to −95° C.
to a compound of formula (VI)

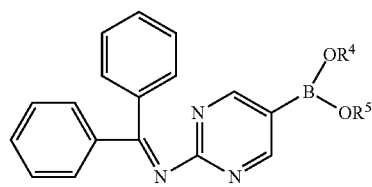

and
c) hydrolyzing the compound of formula (VI) to produce the compound of formula (I)

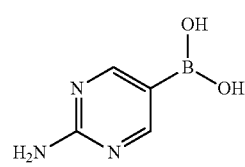

or salts or esters thereof, wherein the mixture of the compound of formula (IV) and the compound of formula (V); and the metalation reagent are added to a reservoir simultaneously.

One embodiment of the invention relates to a process for the preparation of a compound of formula (I)

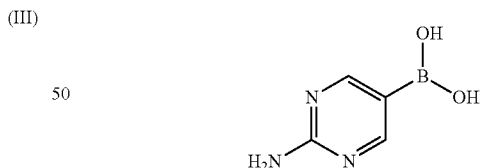

or salts or esters thereof,
characterized in that it comprises the steps of
a) adding a compound of formula (II)

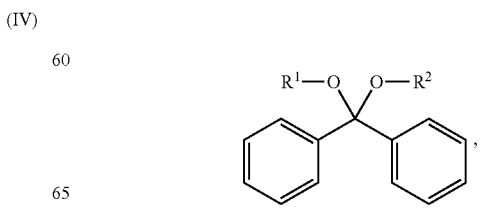

wherein $R^1$ and $R^2$ each independently is $C_{1-6}$ alkyl,
to a solution of a compound of formula (III)

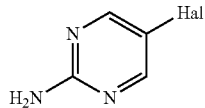
(III)

and a strongly acidic, sulfonic acid, macroreticular polymeric resin in n-butylacetate, wherein Hal is Br;
to form a compound of formula (IV)

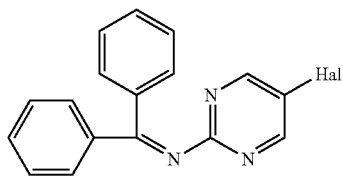
(IV)

and
b) reacting a mixture of a compound of formula (IV) and a compound of formula (V) with a metalation reagent

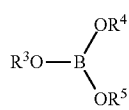
(V)

wherein $R^3$, $R^4$ and $R^5$ each independently is $C_{1-6}$ alkyl;
in THF at a temperature of −90° C. to −95° C.
to a compound of formula (VI)

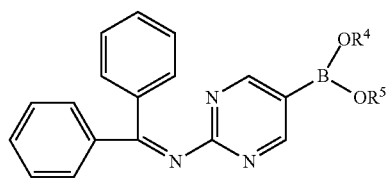
(VI)

and
c) hydrolyzing the compound of formula (VI) to produce the compound of formula (I)

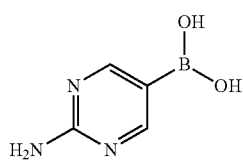
(I)

or salts or esters thereof, wherein such polymeric resin is washed one time or several times with boiling n-butylacetate prior to use and wherein the mixture of the compound of formula (IV) and the compound of formula (V); and the metalation reagent are added in an alternating order or wherein the mixture of the compound of formula (IV) and the compound of formula (V); and the metalation reagent are added simultaneously.

In one embodiment of the invention, the dosing is performed at a temperature of below −90° C.

For the general procedures of steps b) and c) methods known to the person skilled in the art can be used, which can be used under the applied reaction conditions without affecting the other parts of the molecule (US2008/0269523, U.S. Pat. No. 7,196,219B2, Brown, H. C.; Cole, T. E. Organometallics 1983, 2, 1316-1319, Seaman, W. et al. J. Am. Chem. Soc. 1931, 53, 711-723).

If necessary, the reactions can be carried out under dry inert gas such as nitrogen or argon.

If desired, the boronic acid derivative of formula (I) can be converted directly from the reaction mixture into the corresponding ester of formula (I), by esterification with an alcohol. Typically, the boronic ester of formula (I) is prepared by reaction of the boronic acid of formula (I), with an alcohol selected from the group consisting of pinacol, 1,2-ethanediol, and 1,4-butanediol at a pH comprised between 7.0 and 8.5. Typically, the alcohol is pinacol.

The boronic acid (I) and the corresponding ester can be isolated by conventional purification techniques, such as precipitation, and crystallization. In one embodiment of the invention, it is isolated by crystallization in an apolar solvent. Examples of suitable apolar solvents are saturated or unsaturated hydrocarbons, such as hexane, heptane, cyclohexane, toluene, preferably heptane.

Surprisingly, it has now been found that the reaction of 2-amino-5-halogen-pyrimidine of formula (III) to form the corresponding protected compound of formula (IV) works best if a dialkyl ketal (acetal) of formula (II) is used.

Surprisingly, it has now been found that the use of immobilized acidic catalysts, e.g, macroreticular polymeric resins, avoids side-reactions and degradation of educts.

The use of n-butylacetate significantly increases safety of the process in particular for the scaled-up process.

In addition, it has been surprisingly found that the yield in the reaction of the compound of formula (IV) with the borate ester of formula (V) to form 2-amino-pyrimidine-5-boronic acid is increased from 17% to 81% if the process is performed as described above.

In accordance with the above described new process, the following advantages over the known procedures can be provided:
a) The introduction of the protective group via a dialkyl ketal (acetal) does not require expensive organometallic bases and the protected amino group is inert against metalation under the required reaction conditions.
b) The solvents which are used dissolve all compounds to a high degree and are easily removable.
c) A simple, cost-effective and efficient process was developed to convert amino-bromo-pyrimidines into the corresponding boronic acids.
d) The process is easily controllable, robust and scalable.
e) The intermediates of the process can be produced in high purities and can be easily analyzed.
f) The boronic acid compound (I) can be obtained in high purities and high yields.
g) The polymeric catalyst can be easily removed.

The claimed process has the advantage that the reaction rate is higher, the process is easily controllable, and the amount of side-products is low.

The improved process of the invention is therefore useable in technical production of APIs.

The present invention relates to a process for the preparation of a compound of formula (I)

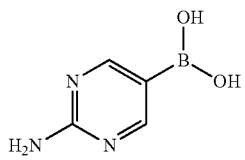
(I)

or salts or esters thereof,
characterized in that it comprises the steps of
a) reacting a compound of formula (II)

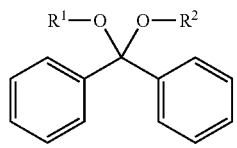
(II)

wherein $R^1$ and $R^2$ each independently is $C_{1-6}$ alkyl
in the presence of an acid with a compound of formula (III)

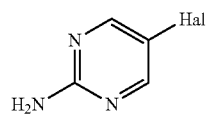
(III)

wherein Hal is F, Cl, Br or I;
to a compound of formula (IV)

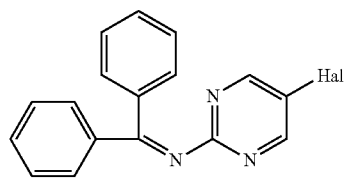
(IV)

and
b) reacting the compound of formula (IV) with a metalation reagent and a compound of formula (V)

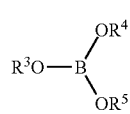
(V)

wherein $R^3$, $R^4$ and $R^5$ each independently is $C_{1-6}$ alkyl;
in a mixture of at least two organic solvents
to a compound of formula (VI)

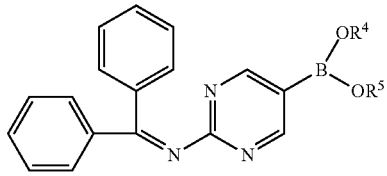
(VI)

and
c) hydrolyzing the compound of formula (VI) to produce the compound of formula (I)

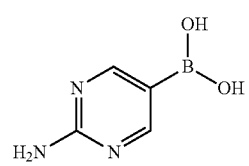
(I)

or salts or esters thereof.

In step a) the 2-amino-5-halogen-pyrimidine of formula (III) is protected through condensation with a highly reactive ketal (acetal) compound of formula (II). By introducing the protective group and forming the imino compound of formula (IV), the amine function cannot be deprotonated in the subsequent metalation step.

In one embodiment of the invention, $R^1$ and $R^2$ are methyl.

In one embodiment of the invention, Hal is Br or I. In one embodiment of the invention, Hal is Br.

In one embodiment of the invention, $R^3$, $R^4$ and $R^5$ are isopropyl.

The dialkyl ketal derivative of formula (II) can be obtained according to methods well known in the art, such as for example the method described in Greene T. W. et al. Protecting groups in Organic synthesis, Wiley, Third Edition.

In one embodiment of the invention, the compound of formula (II) is produced in situ in the reaction mixture by reacting the corresponding benzophenone compound of formula (IIa) with a trialkylorthoformate in the presence of an acid:

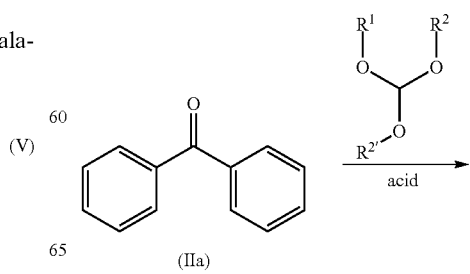
(IIa)

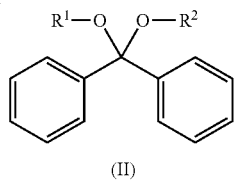

(II)

The dialkyl ketal derivative of formula (II) of the present invention can be isolated or can be used directly in the next step without any further purification.

In one embodiment of the invention, said dialkyl ketal derivative of formula (II) is not isolated but after removal of potentially unreacted starting material and solvent by distillation, said dialkyl ketal derivative is condensed directly with the compound of formula (III).

In one embodiment of the invention, the trialkylorthoformate is trimethylorthoformate.

The acid used in the above reactions is selected from sulfuric acid, hydrochloric acid and a sulfonic acid, such as p-toluene sulphonic acid monohydrate, or p-toluol sulphonic acid ferric.

In one embodiment of the invention, the acid is p-toluene sulphonic acid monohydrate.

In one embodiment of the invention, the conversion of the benzophenone of formula (IIa) to the dialkyl ketal (acetal) of formula (II) is performed in the presence of p-toluene sulphonic acid monohydrate in ethanol or methanol.

In one embodiment of the invention the conversion of the benzophenone of formula (IIa) to the dialkyl ketal (acetal) of formula (II) is performed using trimethylorthoformate and p-toluene sulphonic acid monohydrate in methanol.

In one embodiment of the invention, the reaction of the compound of formula (II) with the compound of formula (III) to produce the protected compound of formula (IV) is performed in a solvent selected from the group consisting of THF, hexane, cyclohexane, heptane, toluene, 1,4-dioxane or mixtures thereof.

In one embodiment of the invention, the reaction of the compound of formula (II) with the compound of formula (III) to produce the protected compound of formula (IV) is performed in 1,4-dioxane. Surprisingly, the use of 1,4-dioxane overcomes the solubility problem for the compound of formula (III). In one embodiment of the invention, the acid is p-toluene sulphonic acid monohydrate.

Surprisingly under the reaction conditions applied, the intermediate imine derivatives of formula (IV) are very stable.

In one embodiment of the invention, the compound of formula (IV) can be isolated by using purification techniques well known to those skilled in the art, such as precipitation and crystallization.

Step b) relates to the conversion of the protected 2-amino-5-halogen-pyrimidine derivative of formula (IV) to the protected compound of formula (VI) via metalation and reaction with a suitable borate ester, e.g. tri-isopropyl borate.

In one embodiment of the invention, the borate ester of formula (V) is added to the mixture prior to the metalation reagent.

In one embodiment of the invention, the borate ester of formula (V) is tri-isopropyl borate.

In one embodiment of the invention, the metalation reagent in step b) is selected from primary or secondary alkyllithium compounds such as butyllithium, hexyllithium or cyclohexyllithium or metallic lithium in the presence of a catalyst.

In one embodiment of the invention, the metalation reagent in step b) is n-butyllithium (n-BuLi).

In one embodiment of the invention, the metalation and the reaction with the borate ester are performed in a temperature range of −50° C. to −90° C. In one embodiment of the invention, the temperature is in the range of −70° C. to −90° C. In one embodiment of the invention such temperature is −75° C. In one embodiment of the invention such temperature is −85° C. In one embodiment of the invention such temperature is −90° C.

In one embodiment of the invention the organic solvents used in the mixtures of at least two organic solvents are aprotic organic solvents. Organic solvents which can be utilized in the mixtures of at least two organic solvents are selected from the group consisting of THF, methyltetrahydrofurane, toluene, 1,4-dioxane, 1,3-dioxane, 1,2-dioxane, hexane, cyclohexane and heptanes.

In one embodiment of the invention, a mixture of two organic solvents is used.

In one embodiment of the invention one of the organic solvents used is THF and the other is toluene.

In one embodiment of the invention, the ratio of the amount of THF and toluene per weight is in the range of 0.3-0.6. In one embodiment of the invention the ratio of THF and toluene is 0.4-0.5. In one embodiment of the invention, the ratio of THF and toluene is 0.44-0.48. In one embodiment of the invention, the ratio of THF and toluene is 0.46.

In one embodiment of the invention, step 1c) is performed without isolation of the compound of formula (VI). In this step the protective group and the ester groups attached to the B-atom are removed by hydrolysis. Both groups can be hydrolyzed simultaneously and/or subsequently. In one embodiment of the invention, the both groups are hydrolyzed simultaneously. In one embodiment of the invention, the both groups are hydrolyzed subsequently and the ester groups attached to the B-atom are hydrolyzed first.

In one embodiment of the invention, the hydrolysis is achieved by the use of aqueous acids. In one embodiment of the invention, the hydrolysis is achieved by hydrolysis by using aqueous sulfuric or hydrochloric acid. In one embodiment of the invention, the hydrolysis is achieved by hydrolysis by using aqueous hydrochloric acid.

In one embodiment of the invention, the hydrolysis takes place in a temperature range of −50° C. to +30° C. In one embodiment of the invention, the hydrolysis takes place at a temperature of −30° C.

In one embodiment of the invention, the 2-amino-pyrimidine-5-boronic acid is isolated as a salt. In one embodiment of the invention the salt is a hydrogen sulfate salt or a hydrochloride salt. In one embodiment of the invention, the compound is isolated as inner salt.

In one embodiment, MTBE is used in one or more steps of steps a), b) or c) in the working up phase.

For the general procedures of steps b) and c) methods known to the person skilled in the art can be used, which can be used under the applied reaction conditions without affecting the other parts of the molecule (US2008/0269523, U.S. Pat. No. 7,196,219B2, Brown, H. C.; Cole, T. E. Organometallics 1983, 2, 1316-1319, Seaman, W. et al. J. Am. Chem. Soc. 1931, 53, 711-723).

If necessary, the reactions can be carried out under dry inert gas such as nitrogen or argon.

If desired, the boronic acid derivative of formula (I) can be converted directly from the reaction mixture into the corresponding ester of formula (I), by esterification with an alcohol. Typically, the boronic ester of formula (I) is prepared by reaction of the boronic acid of formula (I), with an alcohol selected from the group consisting of pinacol, 1,2-ethanediol, and 1,4-butanediol at a pH comprised between 7.0 and 8.5. Typically, the alcohol is pinacol.

The boronic acid (I) and the corresponding ester can be isolated by conventional purification techniques, such as precipitation, and crystallization. In one embodiment of the invention, it is isolated by crystallization in an apolar solvent. Examples of suitable apolar solvents are saturated or unsaturated hydrocarbons, such as hexane, heptane, cyclohexane, toluene, preferably heptane.

Surprisingly, it has now been found that the reaction of 2-amino-5-halogen-pyrimidine of formula (III) to form the corresponding protected compound of formula (IV) works best if the benzophenone compound of formula (IIa) used in such reaction is converted to a dialkyl ketal (acetal) of formula (II) in-situ in the reaction mixture. In addition, it has been surprisingly found that the yield in the reaction of the compound of formula (IV) with the borate ester of formula (V) to form 2-amino-pyrimidine-5-boronic acid is increased from 17% to 65-75% if a mixture of at least two organic solvents is used. Most surprisingly, the best results were obtained using a mixture of toluene and THF.

In accordance with the above described new process, the following advantages over the known procedures can be provided:

a) The introduction of the protective group via a dialkyl ketal (acetal) does not require expensive organometallic bases and the protected amino group is inert against metalation under the required reaction conditions.

b) The solvents which are used dissolve all compounds to a high degree and are easily removable.

c) A simple, cost-effective and efficient process was developed to convert amino-bromo-pyrimidines into the corresponding boronic acids.

d) The process is easily controllable, robust and scalable.

e) The intermediates of the process can be produced in high purities and can be easily analyzed.

f) The boronic acid compound (I) can be obtained in high purities and high yields.

g) The process allows the recovery of benzophenone at the end of the process for re-use.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

"Polar aprotic organic solvents" include borderline polar aprotic organic solvents and mean organic solvents that can accept hydrogen bonds, do not have acidic hydrogen centers and dissolve organic salts. Polar aprotic organic solvents are often essential for reactions that involve strong bases. Examples of such polar aprotic solvents are diglyme, n-butylacetate, 1,4-Dioxane, DMF and DMSO. Examples for borderline polar aprotic organic solvents are THF, Dichloromethane and Ethyl Acetate.

The term "macroreticular" polymeric resins means resins are made of two continuous phases—a continuous pore phase and a continuous gel polymeric phase. The polymeric phase is structurally composed of small spherical microgel particles agglomerated together to form clusters, which, in turn, are fastened together at the interfaces and form interconnecting pores. The surface area arises from the exposed surface of the microgel glued together into clusters. Macroreticular ion exchange resins can be made with different surface areas ranging from 7 to 1500 $m^2/g$, and average pore diameters ranging from 50 to 1,000,000 A. Examples are Amberlyst™ 15 DRY and Amberlyst™ 15 WET (Rohm and Haas Co.).

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $10^{th}$ Ed., McGraw Hill Companies Inc., New York (2001). Any suitable materials and/or methods known to those of skill can be utilized in carrying out the present invention. However, preferred materials and methods are described. Materials and reagents to which reference are made in the following description and examples are obtainable from commercial sources, unless otherwise noted.

The compounds of the invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton. Valence tautomers include interconversions by reorganization of some of the bonding electrons.

Starting materials and reagents for the process for preparation of 2-amino-pyrimidine-5-boronic acid are generally available from commercial sources or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

In one embodiment of the invention, the compound of formula I is used for the preparation of a compound of formula (VII)

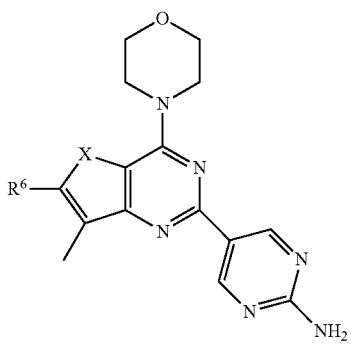

(VII)

wherein
X is O or S;
$R^6$ is

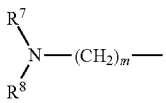

m is 0 or 1;
$R^7$ and $R^8$ form, together with the N atom to which they are attached, a group selected from piperazine, piperidine, pyrrolidine, oxazolidinone, morpholine and thiomorpholine, which group is optionally substituted with —C(=Y)$R^9$;
Y is O or S;
$R^9$ is —$C_{1-12}$ alkyl optionally substituted by OH.

In one embodiment of the invention, the process described above is used, wherein the compound of formula I is used in a Suzuki-coupling reaction for the preparation of a compound of formula VII

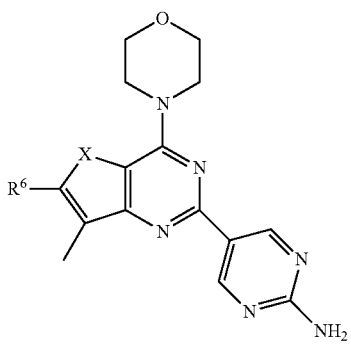

(VII)

wherein
X is O or S;
$R^6$ is

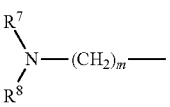

m is 0 or 1;
$R^7$ and $R^8$ form, together with the N atom to which they are attached, a group selected from piperazine, piperidine, pyrrolidine, oxazolidinone, morpholine and thiomorpholine, which group is optionally substituted with —C(=Y)$R^9$;
Y is O or S;
$R^9$ is —$C_{1-12}$ alkyl optionally substituted by OH.

Such Suzuki-coupling reactions are for example disclosed in WO 2014/056955.

The following abbreviations were used in the description and the claims:

THF tetrahydrofuran
DMA Dimethylamine
DMF Dimethylformamide
MTBE Methyl tert-butyl ether
iprop iso-propyl

EXAMPLES

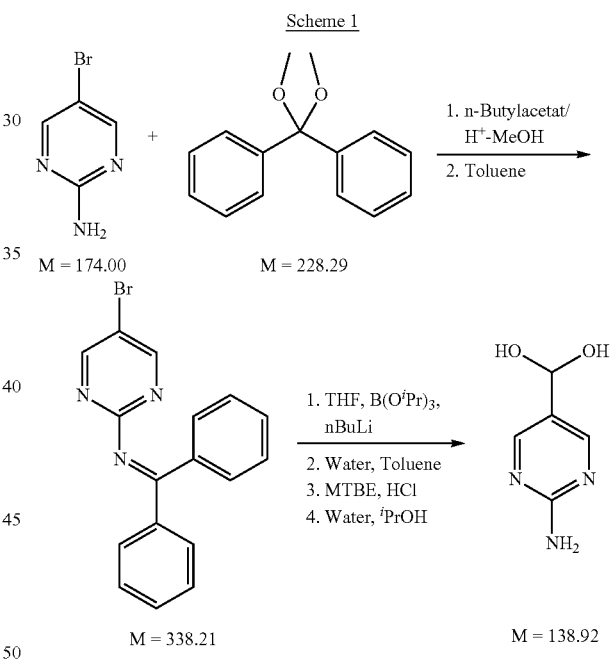

Scheme 1 summarizes one example for the process of the invention.

Amino protected compounds were prepared by reacting a dialkyl ketal (acetal) derivative with a 2-amino-5-halo-pyrimidine compound in the presence of an immobilized acidic catalyst, like Amberlyst™ 15 DRY. The halogen (Hal) was typically Br. The protected imine compound was reacted with a borate ester and a metalation agent. Typically, an alkyl-lithium compound, such as n-butyllithium, was used in such metalation. The borate ester used was typically tri-isopropyl borate.

The following schemes, Schemes 2-9, further illustrate chemical reactions, processes, methodology for the synthesis of 2-amino-pyrimidine-5-boronic acid pyrimidine of formula (I), and certain intermediates and reagents.

Scheme 2

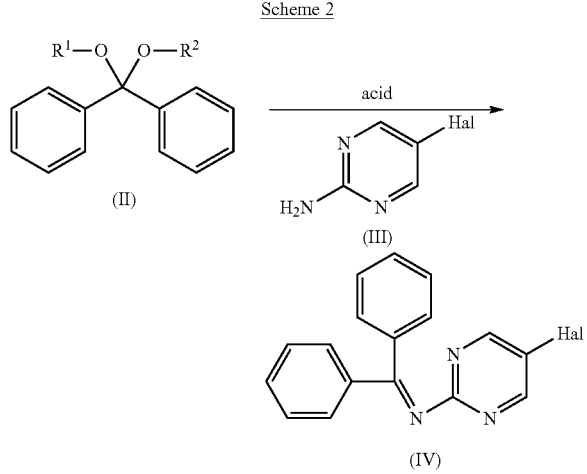

Amino protected compounds of general formula (IV) were prepared by reacting a dialkyl ketal (acetal) derivative of formula (II) with a 2-amino-5-halo-pyrimidine compound of formula (III) in the presence of an acid catalyst, like p-toluene sulfonic acid monohydrate. The halogen (Hal) was typically Br.

Scheme 3

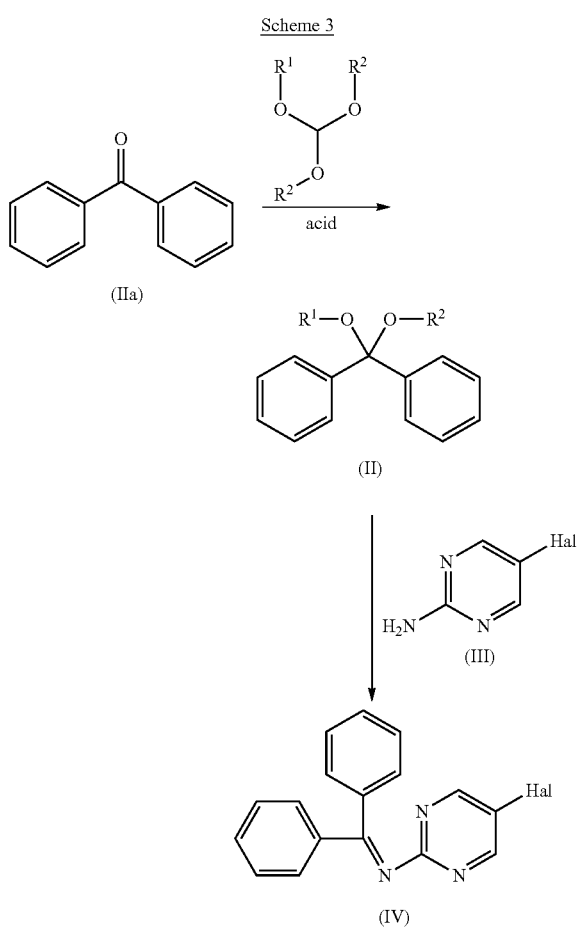

Dialkyl ketal (acetal) compounds of formula (II) were typically prepared in situ in the reaction mixture by reacting a benzophenone compound of formula (IIa) with a trialkylorthoformate in the presence of an acid catalyst. Typically, trimethylorthoformate was used in the presence of p-toluene sulfonic acid monohydrate. Typically, the halogen (Hal) was Br. Typically, the first reaction step is performed in Methanol and the second reaction step in 1,4-dioxane.

Scheme 4

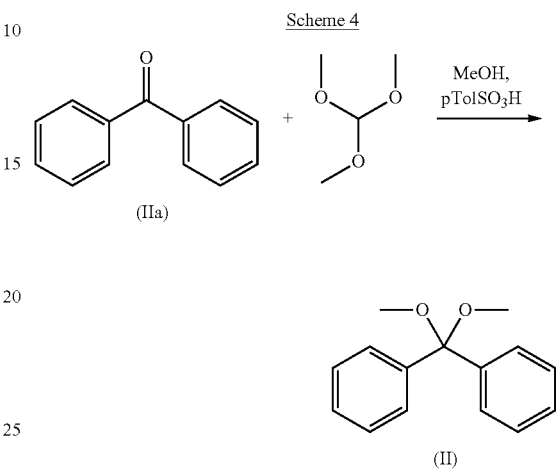

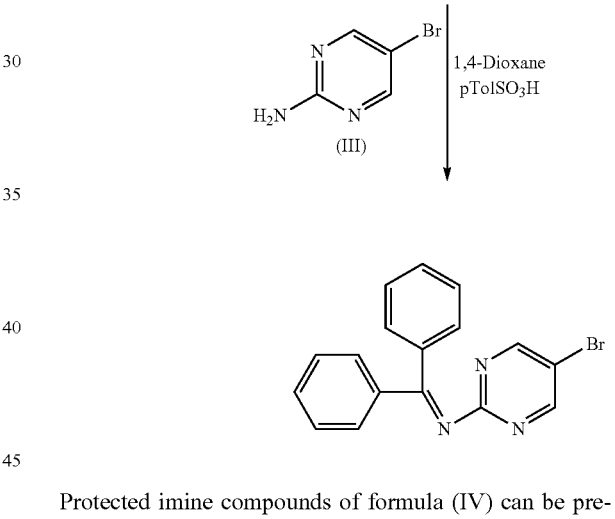

Protected imine compounds of formula (IV) can be prepared in a two-step reaction. In step 1, a benzophenone compound of formula (IIa) is reacted with trimethylorthoformate in the presence of p-toluene sulfonic acid monohydrate in methanol to form dialkyl ketal (acetal) (II). In step 2, the dialkyl ketal (acetal) compound of formula (II) is reacted with 2-amino-5-bromo-pyrimidine in 1,4-dioxane.

Scheme 5

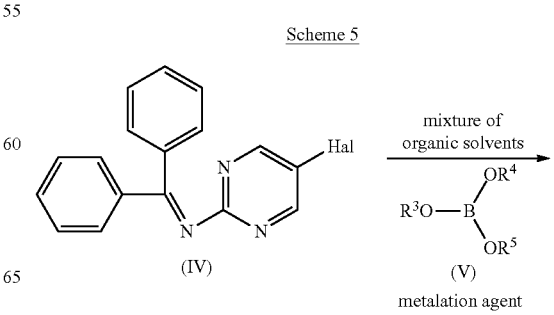

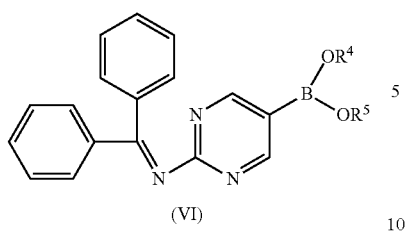

The protected imine compound of formula (IV) was reacted with a borate ester (V) and a metalation agent. Typically, an alkyllithium compound, such as n-butyllithium, was used in such metalation. The borate ester (V) used was typically tri-isopropyl borate. The aforementioned reactions were performed in a mixture of at least two organic solvents. Typically a mixture of THF and toluene was used. The typical ratio of THF and toluene was in the range of 0.3-0.6. The temperature of the reaction was typically in the range of −50° C. to −100° C. Typically, the borate ester (V) is added to the reaction mixture prior to the metalation agent.

Scheme 6

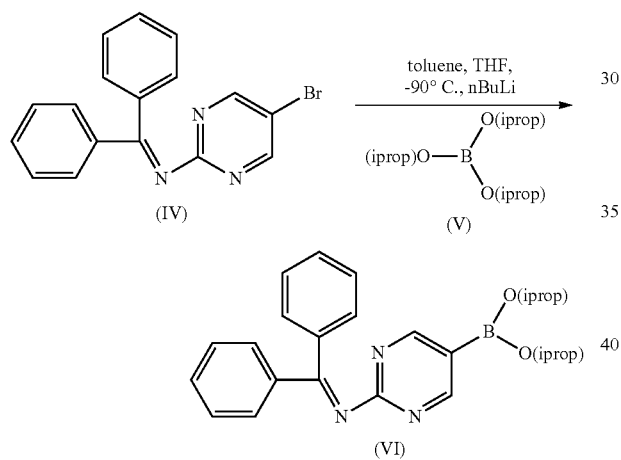

The protected imine compound of formula (IV) was reacted with n-butyllithium as a metalation agent. Typically, the metalation reagent was added after the tri-isopropyl borate of formula (V). The conversions were performed in a mixture of THF and toluene. The typical ratio of THF and toluene was in the range of 0.3-0.6. The temperature of the reaction was typically in the range of −50° C. to −100° C., typically −90° C.

Scheme 7

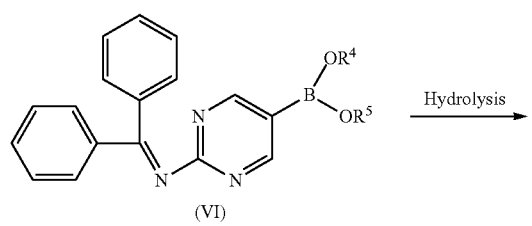

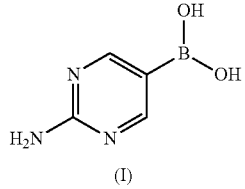

The protected imine compound of formula (VI) was hydrolyzed to form 2-amino-pyrimidine-5-boronic acid (I). In this step the protective group and the boronic acid ester groups were cleaved by hydrolysis typically using aqueous sulfuric or hydrochloric acid.

Scheme 8

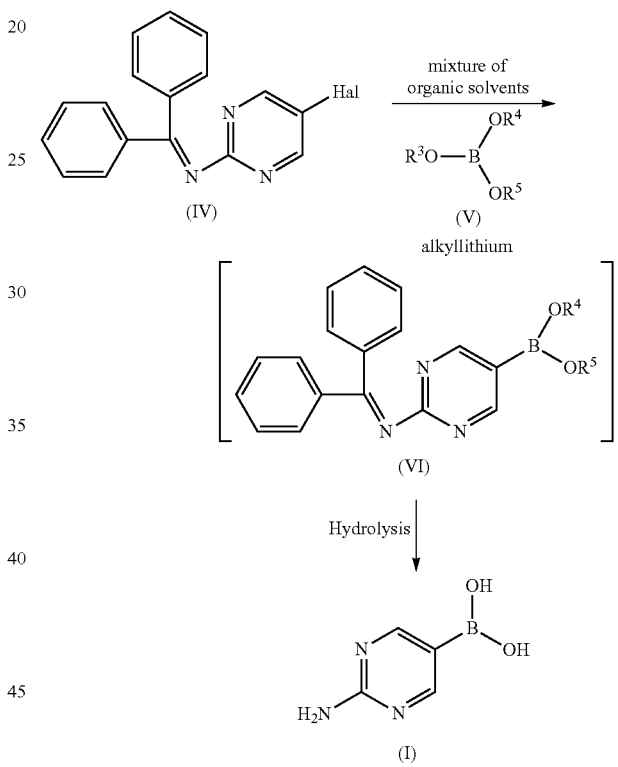

The protected imine compound of formula (IV) was reacted with an alkyllithium as a metalation agent. The conversions were performed in a mixture of at least two organic solvents. Typically, the borate ester was added to the reaction mixture prior to the metalation agent to form the protected boronic acid methyl ester of formula (VI). The conversions were typically performed in a mixture of THF and toluene. The typical ratio of THF and toluene was in the range of 0.3-0.6. The temperature of the reaction is typically in the range of −50° C. to −100° C., typically −90° C. Typically, the compound of formula (VI) was not isolated prior to hydrolysis to the compound of formula (I). The protected imine compound of formula (VI) was hydrolyzed to form 2-amino-pyrimidine-5-boronic acid (I). In this step the protective group and the boronic acid ester groups were cleaved by hydrolysis typically using aqueous sulfuric or hydrochloric acid.

Scheme 9

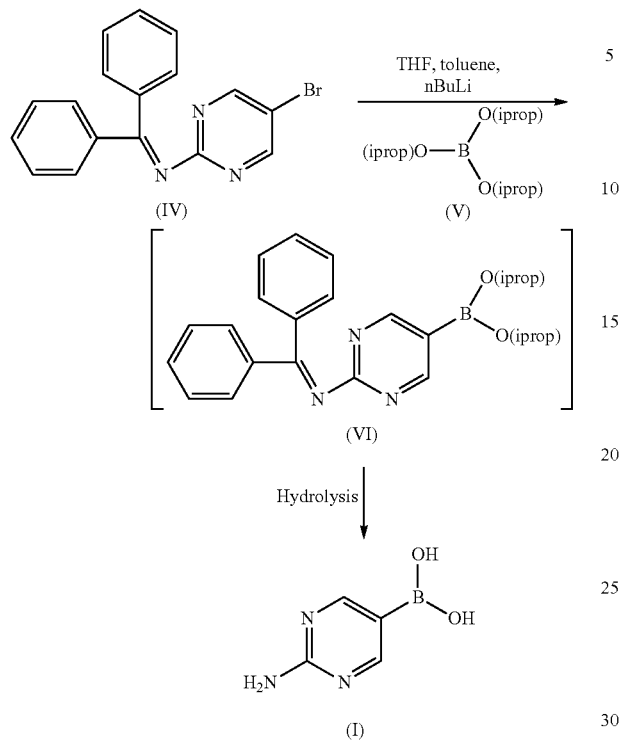

The protected imine compound of formula (IV) was reacted with n-butyllithium as a metalation agent. The metalation reagent was typically added to the reaction mixture after the tri-isopropyl borate of formula (V). The conversions were performed in a mixture of at least two organic solvents. The conversions were performed in a mixture of THF and toluene. The typical ratio of THF and toluene was in the range of 0.3-0.6. The temperature of the reaction was typically in the range of −50° C. to −100° C., typically −90° C. Typically, the compound of formula (VI) was not isolated prior to hydrolysis to the compound of formula (I). The protected imine compound of formula (VI) was hydrolyzed to form 2-amino-pyrimidine-5-boronic acid (I). In this step the protective group and the boronic acid ester groups were cleaved by hydrolysis typically using aqueous sulfuric or hydrochloric acid.

Example 1

Benzhydrylidene-(5-bromo-pyrimidine-2-yl)-amine

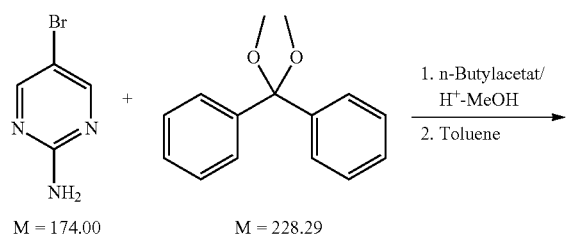

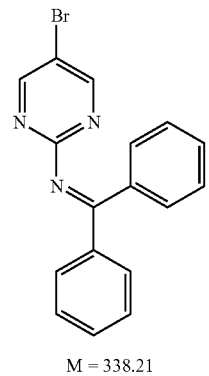

M = 338.21

In a clean, dry and jacket reactor (rendered inert) with distillation equipment, 200 g 2-amino-5-bromo-pyrimidine and 5.43 g washed Amberlyst™ 15 (H$^+$ form) are charged at room temperature and suspended in 751 g n-butylacetate. The stirrer is switched on, approximately 300 rpm. A light stream of nitrogen is bubbled through the mixture via an inlet tube. In a suitable glass vessel 294 g dimethoxydiphenylmethane are dissolved in 2253 g n-butylacetate. The solution is transferred to a reservoir vessel. The jacket temperature is adjusted to maintain an internal temperature of 114-120° C. in the reactor. Subsequently, the addition of the prior prepared solution is started. The addition takes about 5 to 6 hours. The internal temperature should stay between 114° C. to 120° C. Distillate is collected. After the addition is complete, the batch is stirred at the given temperature and distillate is collected until full conversion is reached. Ratio product: precursor >99:1. In total 731 g distillate are collected. The internal temperature is adjusted to 75 to 85° C. The obtained thin suspension is now transferred into a second dry, clean reactor (which was rendered inert) via a polish filtration cartridge to remove the catalyst residue. A clear, yellow solution is obtained in which a temperature of 75° C. is maintained. The reaction vessel is purged with n-butylacetate and following a visual control, the solution is transferred back to it. Subsequently, the temperature is lowered to 60 to 70° C. while crystallisation of the product occurs. Vacuum is applied (approximately 130 mbar) and a total amount of 1530 g of second distillate are collected. A coarse crystalline suspension is obtained. The vessel is vented with nitrogen and the batch is cooled to room temperature (18-22° C.). Stirring is continued for additional 30 min and subsequently the product is filtered using a standard porcellaine filter Nutsche. The crude wetcake is dried in a tray drier at 40-50° C. and 100 to 200 mbar during 20 hours. One obtains 329 g of a yellow, crystalline crude product (corresponds to 85%). The crude material is charged to a clean, dry and inert reactor and 3600 g toluene is added. The mixture is stirred for 90 to 120 min at a temperature of 25 to 30° C. until a thin suspension is formed. It is filtered using a cartridge charged with carbon black into another dry and clean reactor. A clear, bright yellow solution is obtained. Vacuum is applied (130-140 mbar) and the temperature is adjusted to 50 to 55° C. to collect distillate. In total, 3029 g of third distillate are collected. In the residue, a thick suspension is formed. The vessel is vented with nitrogen and the mixture is cooled to room temperature (18 to 22° C.). The obtained suspension is filtered using a porcelain filter. One obtains 316 g of wet pure product, which is dried in a tray drier at 40 to 50° C. and 100 to 200 mbar within 20 hours. Finally, 291 g of a colourless to bright yellow fine crystalline solid are obtained (75%).

$^1$H-NNR (400 MHz, dmso-d6)
δ=7.15-7.73 (m, 10H), 8.73 (s, 2H)
MP: 162-165° C.
MS (El+): M/Z=337

Example 2

2-amino-pyrimidine-5-boronic acid

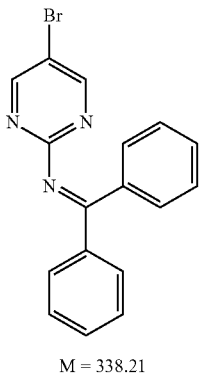

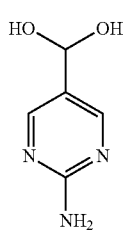

M = 338.21

M = 138.92

To a dry, clean jacket reactor (which was rendered inert, nitrogen atmosphere) with mechanical stirring, electronic thermometer, and two reservoirs (dropping funnels) are charged 804 g dry THF and cooled to −95° C. In one of the reservoirs (R1) a solution of 172 g benzhydrylidene-(5-bromo-pyrimidin-2-yl)-amine, 115 g triisopropylborate (1.2 eq.) and additional 1609 g THF is prepared. To the second dropping funnel (R2) are charged 155 g n-butyllithium (2.5M, 1.1 eq.). Now from R1, 568 g solution (0.3 eq.) are added dropwise, maintaining a temperature below −90° C. Subsequently, 21.1 g of n-butyllithium solution from R2 (0.15 eq.) are added, again maintaining the temperature below −90° C. Then, another 284 g solution from R1 (0.15 eq.) are added followed by 21.1 g n-BuLi from R2 (0.15 eq.). The procedure is repeated again by the addition of 284 g solution from R1 (0.15 eq.) and subsequently 21.2 g n-BuLi from R2 (0.15 eq.). The conversion is monitored by HPLC. One continues with addition of 284.0 g solution from R1 (0.15 eq.) followed by 21.1 g n-BuLi from R2 (0.15 eq.). At this point in total 0.75 eq. of the precursor and 0.6 eq. n-BuLi have been added. Additional 284.0 g solution from R1 (0.15 eq.) followed by 21.1 g n-BuLi (0.15 eq.) are added. The conversion is checked by HPLC again. Additional 190 g solution from R1 (0.1 eq.) and 35.3 g n-BuLi (0.25 eq.) are added. The batch is analyzed per HPLC again. Another 14.1 g n-BuLi (0.1 eq.) may need to be added. The batch is warmed to −60° C. and quenched onto 1540 g water. The reaction mixture is allowed to warm to room temperature and stirred for at least 30 min. 1125 g Toluene are added and the batch is stirred for further 15 min. The layers are separated and the aqueous is extracted again with 510 g toluene. To the aqueous product layer, 563 g MTBE are added and the pH is adjusted to about 1.3 by addition of about 200 g 20% hydrochloric acid. Now the batch is allowed to stir for at least 4 hours and subsequently, the layers are separated. The aqueous layer is extracted with 563 g MTBE and after the layers are separated[7] the pH is adjusted using 65.0 g 33% caustic soda lye to roughly 7.5. The obtained slurry is stirred for one hour at room temperature and filtered. 126 g of a white crude product containing residual moisture is obtained. It is reslurried in 395 g water and 95.0 g Isopropanol. The mixture is warmed to 50° C. and stirred for at least one hour at this temperature. The batch is cooled to room temperature and the fine product is filtered. A wet fine product is obtained, which is dried in a tray drier at 40° C. to 45° C. and 100 to 200 mbar leaving 57.6 g of the white, fine crystalline boronic acid (81%).

$^1$H-NNR (400 MHz, dmso-d6+D$_2$O)
δ=6.82 (s, 2H), NH$_2$, B(OH)$_2$ not observed due to H-D exchange.
MP: 186-188° C.

Example 3

Benzhydrylidene-5-(bromo-pyrimidine-2-yl)-amine

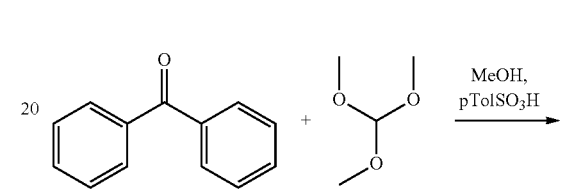

(IIa)
M = 182.22

M = 106, 12

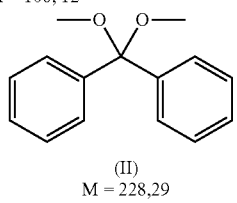

(II)
M = 228,29

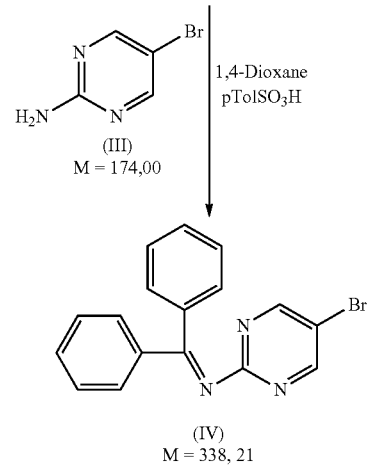

(III)
M = 174,00

(IV)
M = 338, 21

In a suitable flask with distillation bridge, 200 g Benzophenone (1.1 mol, 1.2 eq.) was added to 1860 g Methanol (2350 ml) under stirring. To the reaction mixture, p-Toluene sulfonic acid monohydrate (4 g, 21 mmol) was added at room temperature under stirring. The mixture was heated to reflux temperature (65° C.). Within 2 hours Trimethylorthoformate (175 g, 1.65 mol) was added under stirring while a mixture of Methanol and Methylformate was distilled off. About 190 to 210 g of distillate was collected at head temperature 58° C. After the addition was complete, the mixture was stirred for another 60 min. Subsequently, the temperature was slowly raised to 100° C. and further distillate (3040 g) was collected while 1,4-dioxane (3200 g, 3100 ml) was added in parallel. The reaction mixture is cooled to 80° C. and 160 g (0.92 mol) 2-amino-5-bromo-pyrimidine was added under stirring. After addition of the 2-amino-5-bromo-pyrimidine, the reaction mixture is heated to 100° C. and a mixture of Methanol and 1,4-dioxane was distilled off. The filling level of the reaction flask is continuously checked and if necessary, 1,4-Dioxane added to keep the filling level constant. After completion of the reaction (after approximately 16 hours, the conversion remained static), further 1,4-Dioxane is distilled (a net amount of 1440 g of solvent is removed from the mixture) and the batch is cooled while a suspension is formed. At approx. 60° C., MTBE (480 g, 650 ml) is added and the slurry is slowly cooled to room temperature (20-25° C.). The solid was filtered and the residue washed with 80 g of MTBE. After drying at 40° C. and 200 mbar over night in a tray drier, 246.9 g (80%) of the crude product with a purity of 98-99% was obtained.

$^1$H-NNR (400 MHz, dmso-d6)
δ=7.15-7.73 (m, 10H), 8.73 (s, 2H)
MP: 162-165° C.
MS (El+): M/Z=337
Visual: white to beige solid.

Example 4

2-amino-pyrimidine-5-boronic acid

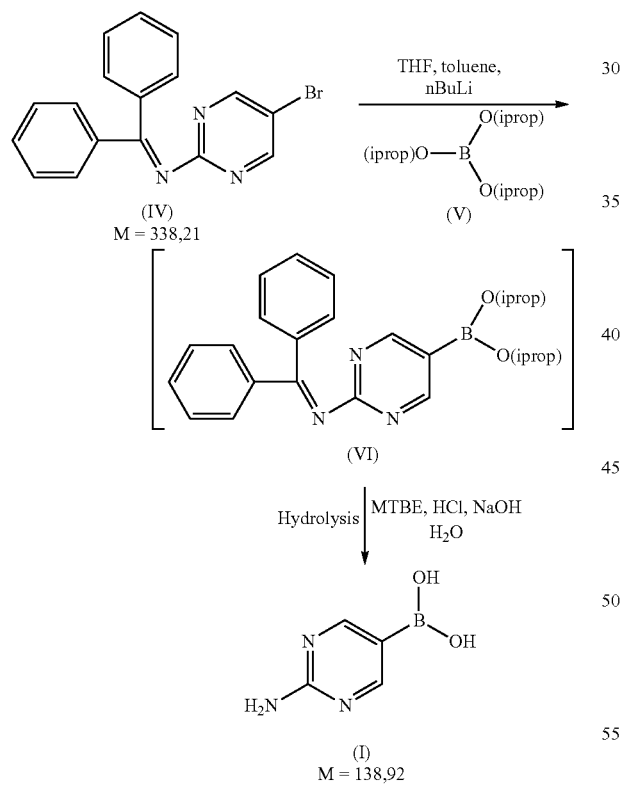

In a suitable flask, Benzhydrylidene-5-(bromo-1,2-dihydro-pyrimidine-2-yl)-amine (25 g, 74 mmol), THF (139 g, 158 ml) and Toluene (302 g, 343 ml) were mixed and cooled to −90° C. To this mixture Tri-isopropylborate (15.3 g, 81 mmol) was added at once. Slowly, over a period of 2 hours n-BuLi (24.7 g, 89 mmol) was added maintaining the temperature below −90° C. After full conversion was confirmed, the reaction mixture was warmed up to −30° C. and transferred to a second flask containing 213 g of water at 20 to 25° C. The biphasic mixture was stirred for another 30 min and subsequently, the layers were separated. The aqueous phase was set to pH 1 by adding 37% HCl. The aqueous phase is extracted twice with MTBE (80 g, 108 ml each) and the obtained aqueous phase set to pH 7.5 applying 33% aqueous NaOH to precipitate the crude product. After filtration, washing with 15 g of water and drying in the drying chamber 7.1 g (51 mmol, 69%) of the final product is obtained.

$^1$H-NNR (400 MHz, dmso-d6+D$_2$O) δ=6.82 (s, 2H), NH$_2$, B(OH)$_2$ not observed due to H-D exchange. MP: 186-188° C. Visual: white to off-white solid.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:

1. A process for the preparation of a compound of formula (I)

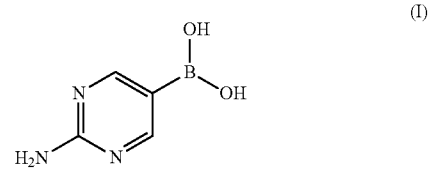

or salts or esters thereof, comprising
a) adding a compound of formula (II)

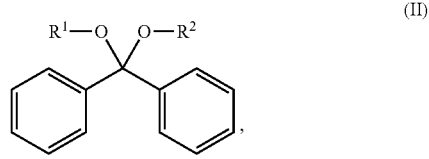

wherein R$^1$ and R$^2$ each independently is C$_{1-6}$ alkyl,
to a solution of a compound of formula (III)

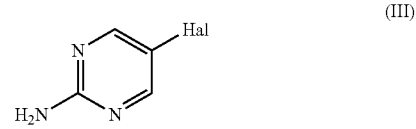

and an immobilized acidic catalyst in a polar aprotic organic solvent with a boiling point above 100° C., wherein Hal is F, Cl, Br or I;

to form a compound of formula (IV)

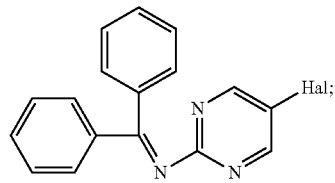

b) reacting a mixture of a compound of formula (IV) and a compound of formula (V) with a metalation reagent

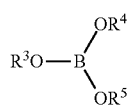

wherein $R^3$, $R^4$ and $R^5$ each independently is $C_{1-6}$ alkyl;
in a polar aprotic organic solvent at a temperature of −90° C. to −95° C.
to a compound of formula (VI)

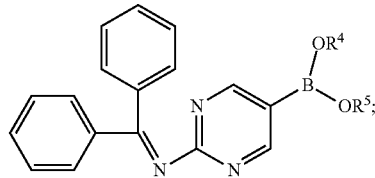

and
c) hydrolyzing the compound of formula (VI) to produce the compound of formula (I)

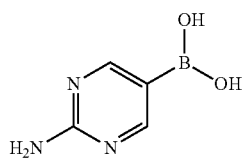

or salts or esters thereof.

2. The process of claim 1, wherein the polar aprotic organic solvent in step a) has a boiling point in the range of 120° C. to 130° C.

3. The process of claim 1 wherein the polar aprotic organic solvent in step a) is n-butylacetate.

4. The process of claim 1 wherein the polar aprotic organic solvent in step b) is THF.

5. The process of claim 1, wherein the immobilized acidic catalyst is a solid polymeric resin.

6. The process of claim 1, wherein the immobilized acidic catalyst is a solid macroreticular polymeric resin.

7. The process of claim 1, wherein the immobilized acidic catalyst is a solid macroreticular polymeric ion exchange resin.

8. The process of claim 1, wherein the immobilized acidic catalyst is a solid, strongly acidic, macroreticular polymeric ion exchange resin.

9. The process of claim 1, wherein the immobilized acidic catalyst is based on crosslinked styrene divinylbenzene copolymers.

10. The process of claim 1, wherein the immobilized acidic catalyst is Amberlyst™.

11. The process of claim 1, wherein the immobilized acidic catalyst is Amberlyst™ 15 DRY.

12. The process of claim 1, wherein the immobilized acidic catalyst is washed one time or several times n-butylacetate prior to use.

13. The process of claim 1, wherein the compound of formula (II) is dissolved in n-butylacetate.

14. The process of claim 1, wherein Hal is Br.

15. The process of claim 1, wherein the metalation reagent is n-butyllithium.

16. The process of claim 1, wherein $R^3$, $R^4$ and $R^5$ are isopropyl.

17. The process of claim 1, wherein the mixture of the compound of formula (IV) and the compound of formula (V); and the metalation reagent are added in an alternating order.

18. The process of claim 1, wherein the mixture of the compound of formula (IV) and the compound of formula (V); and the metalation reagent are added simultaneously.

19. The process of claim 17 claim 1, wherein the dosing is performed at a temperature of −95° C. to −90° C.

* * * * *